United States Patent [19]

Suzuki et al.

[11] Patent Number: 4,673,393
[45] Date of Patent: * Jun. 16, 1987

[54] MEDICAL INSTRUMENT

[75] Inventors: Tatsuo Suzuki, Machida; Atsushi Matsumoto, Fuji, both of Japan

[73] Assignee: Terumo Kabushiki Kaisha, Tokyo, Japan

[ * ] Notice: The portion of the term of this patent subsequent to Sep. 9, 2003 has been disclaimed.

[21] Appl. No.: 813,025

[22] Filed: Dec. 24, 1985

[30] Foreign Application Priority Data

Dec. 28, 1984 [JP] Japan ................................ 59-281077

[51] Int. Cl.$^4$ ............................................ A61M 25/00
[52] U.S. Cl. ...................................... 604/167; 604/256
[58] Field of Search .................... 604/167, 30, 99, 169, 604/174, 175, 201, 213, 215, 237, 244, 256, 411, 905; 128/DIG. 26

[56] References Cited

U.S. PATENT DOCUMENTS

| | | | |
|---|---|---|---|
| 3,853,127 | 12/1974 | Spademan | 604/167 |
| 4,000,739 | 1/1977 | Stevens | 604/167 |
| 4,143,853 | 3/1979 | Abramson | 604/237 |
| 4,177,814 | 12/1979 | Knepshield et al. | 604/167 |
| 4,244,379 | 1/1981 | Smith | 604/237 |
| 4,412,836 | 11/1983 | Brignola | 604/237 |
| 4,430,081 | 2/1984 | Timmermans | 604/167 |
| 4,436,519 | 3/1984 | O'Neill | 604/256 |
| 4,475,548 | 10/1984 | Muto | 604/167 |
| 4,610,665 | 9/1986 | Matsumoto et al. | 604/167 |
| 4,610,674 | 9/1986 | Suzuki et al. | 604/167 |
| 4,626,245 | 12/1986 | Weinstein | 604/167 |

FOREIGN PATENT DOCUMENTS

| | | |
|---|---|---|
| 3042229 | 5/1982 | Fed. Rep. of Germany . |
| 57-110262 | 9/1982 | Japan . |
| 59-133877 | 1/1984 | Japan . |
| 59-131364 | 7/1984 | Japan . |
| 59-131366 | 7/1984 | Japan . |
| 59-164067 | 9/1984 | Japan . |
| 59-155255 | 9/1984 | Japan . |
| 60-88562 | 5/1985 | Japan . |
| 2135889 | 9/1984 | United Kingdom . |

*Primary Examiner*—C. Fred Rosenbaum
*Assistant Examiner*—Gene B. Kartchner
*Attorney, Agent, or Firm*—Frishauf, Holtz, Goodman & Woodward

[57] ABSTRACT

A medical instrument having a path for receiving a bar-like member and a combination of valves provided in the path. The combination of valves comprises a first disc-like valve having a first slit open only to one of the end faces thereof and a second slit open only to the other of the end faces thereof, the first and second slits crossing each other to form a distance of intersection inside the first valve, and a second disc-like valve disposed in parallel to the first valve and having a slit opening to both end faces thereof. The slit of the second valve crosses the intersection point of the first valve so that the bar-like member passes through the slit of the second valve as well as the intersection of the first valve when it is inserted.

10 Claims, 26 Drawing Figures

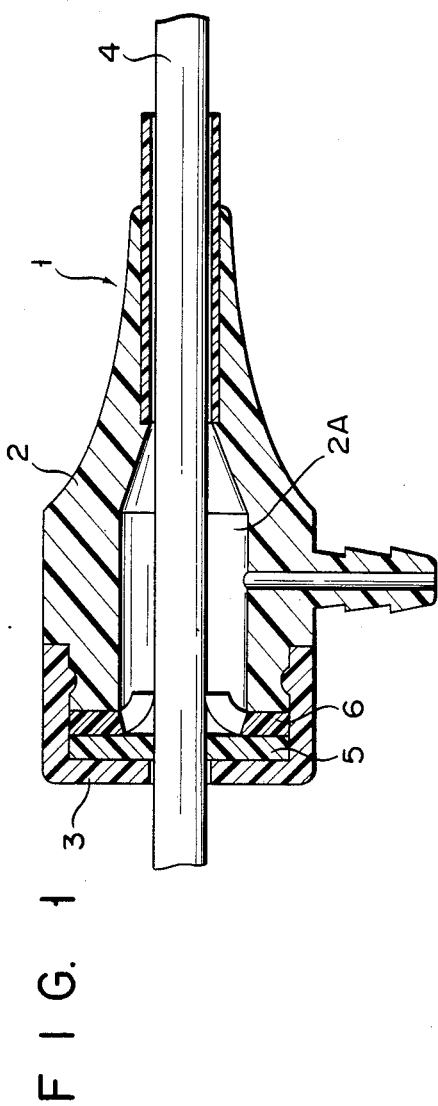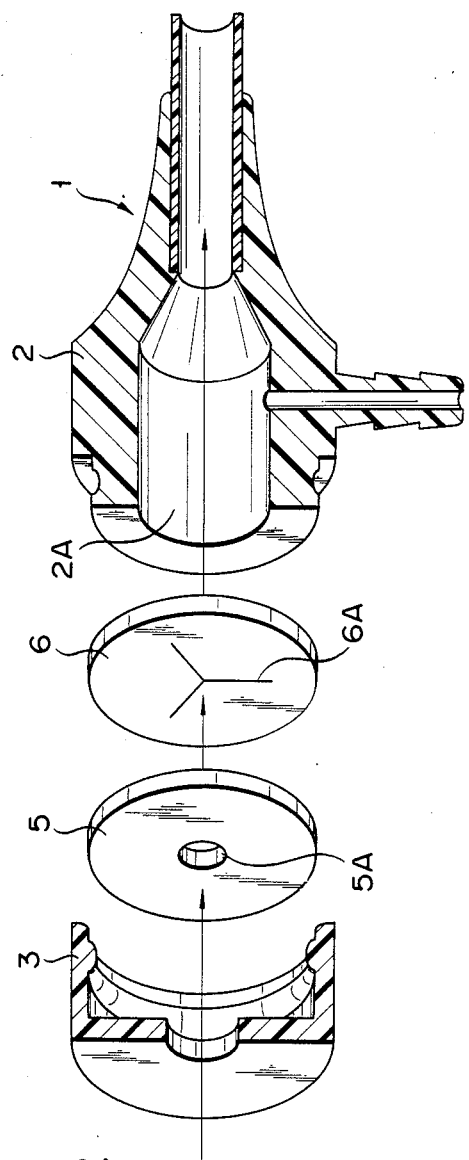
FIG. 1
FIG. 2

FIG. 5A   FIG. 5B   FIG. 5C
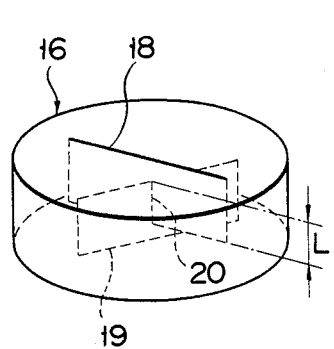
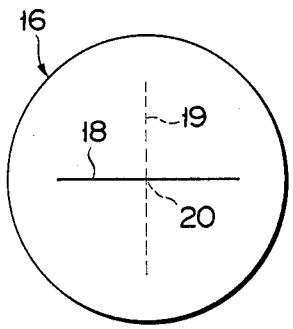
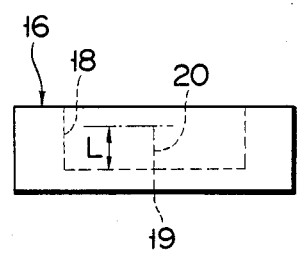
FIG. 6
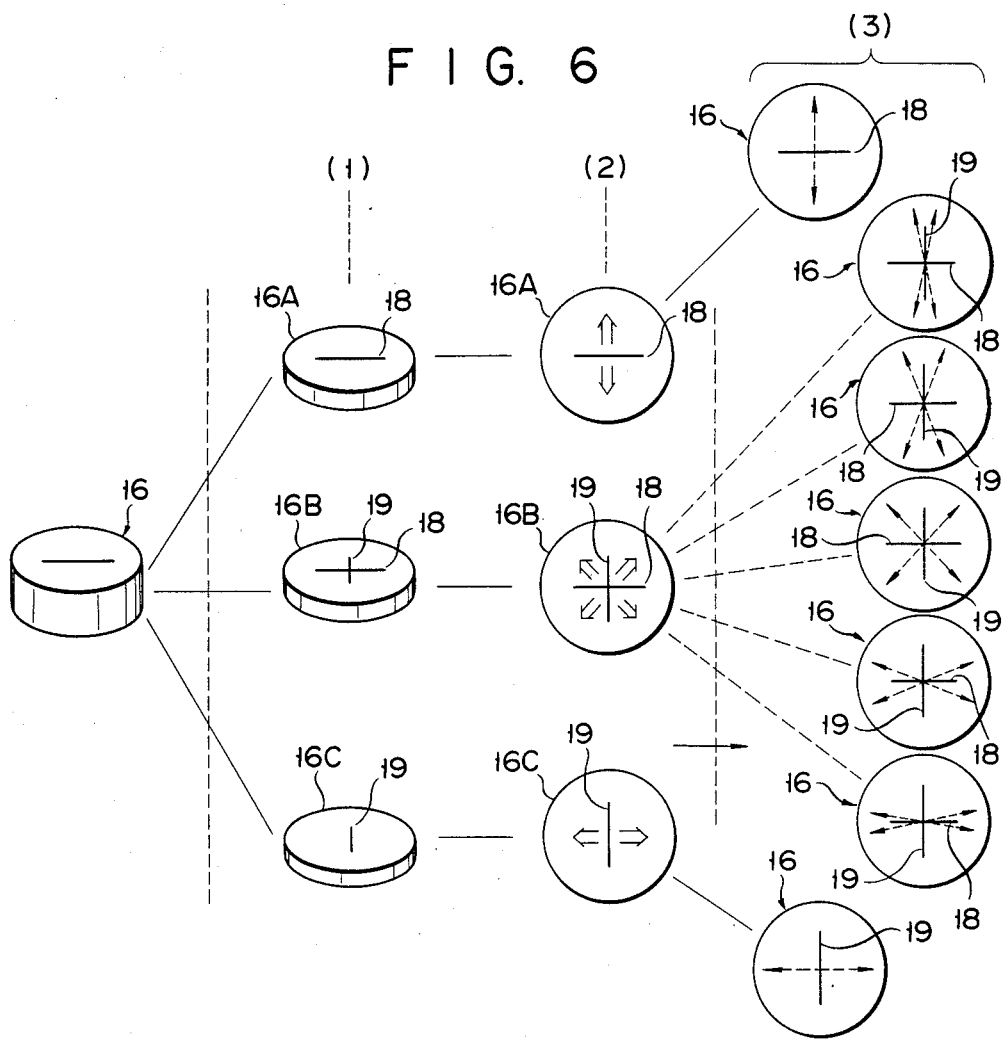

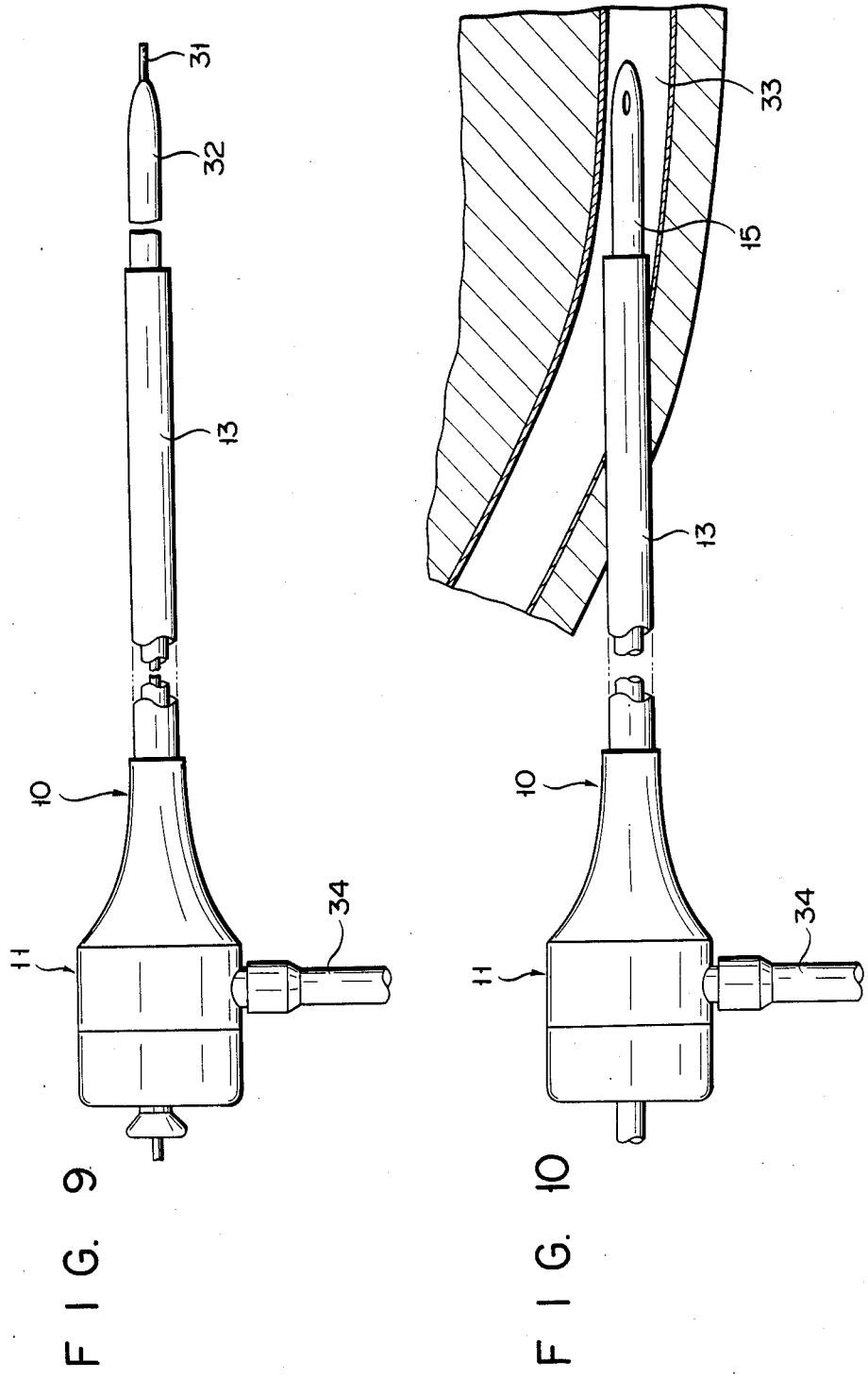

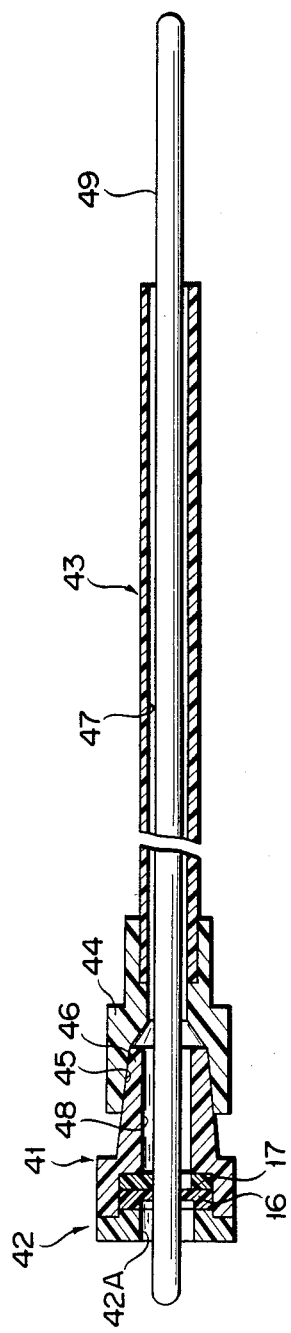
F I G. 11
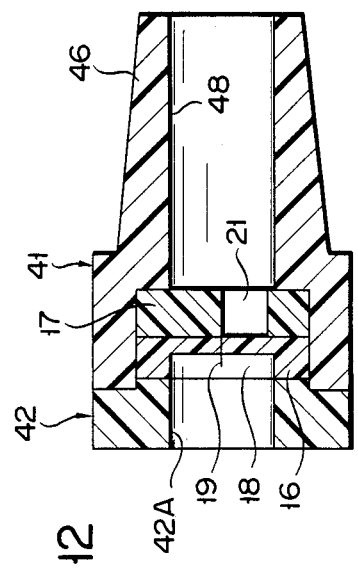
F I G. 12

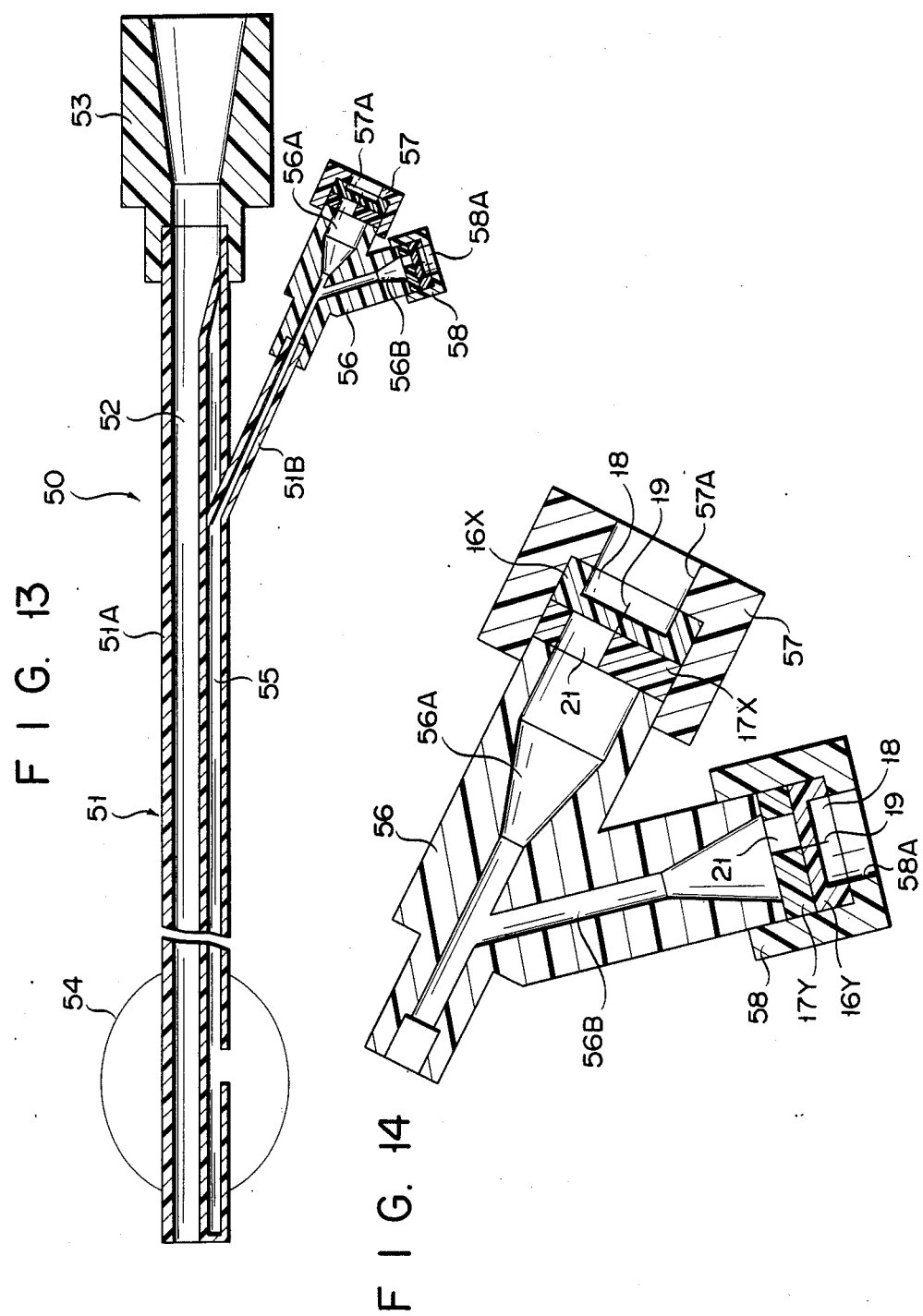

F I G. 15
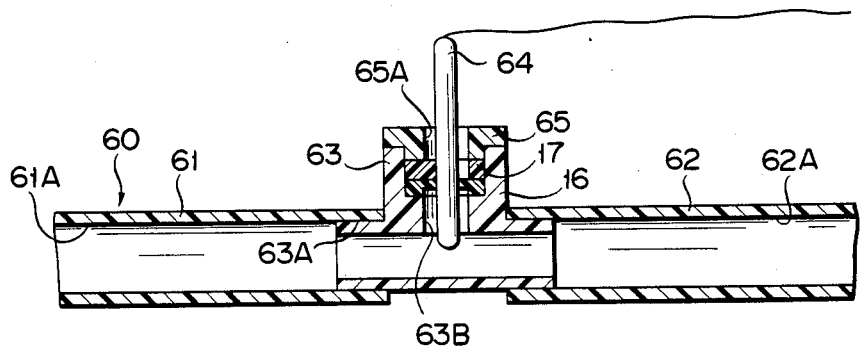
F I G. 16
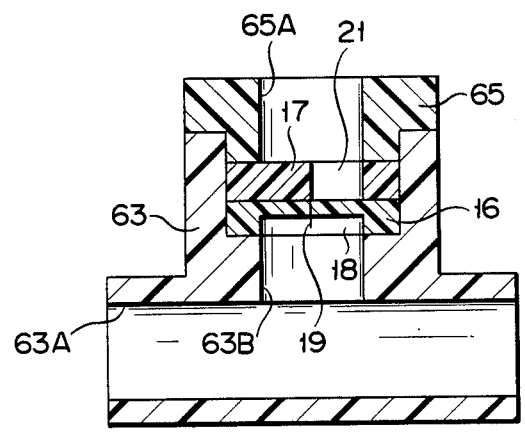

MEDICAL INSTRUMENT

BACKGROUND OF THE INVENTION

1. Field of the Invention

This invention relates to medical instruments provided with valve means, and more particularly to a medical instrument suitable for use in a catheter introducer, a general catheter, a catheter with a balloon, an ectosomatic circulating device and the like.

2. Description of the Prior Art

There has heretofore been used a catheter introducer for medical treatment as a means for introducing rod-like members such for example as a catheter for blood-vessel contrast and the like into a blood-vessel. In a method of introducing a catheter using a catheter introducer into a blood-vessel, firstly, a hollow needle inserted therethrough with an inner needle penetrates through a skin and is introduced into the blood-vessel, subsequently, and a guide wire is inserted through the hollow needle, from which the inner needle is removed, and thereafter, the hollow needle is removed and only the guide wire is left behind. Subsequently, a main body of the introducer inserted therethrough with an expander is advanced into the blood-vessel through the guide wire, thereafter, the dilator together with the guide wire, and the catheter is guided into a path in a main body so as to be insertable into the blood-vessel.

In the catheter introducer for medical treatment as described above, when the catheter is inserted into a path of the main body of the introducer and when the catheter is not inserted, in order to prevent a blood flow to the outside through the path of the main body of the introducer, it is necessary to provide a valve body in the path of the main body of the introducer.

In FIGS. 1 and 2, designated at reference numeral 1 is a catheter introducer for medical treatment, 2 a main body, 3 a cap, and 4 a catheter. In this catheter introducer 1, a first valve body 5 and a second valve body 6, which are made of an elastomeric material, are parallelly provided in a path 2A of the main body 2 in a manner to be clamped by the main body 2 and the cap 3. The first valve body 5 is provided at the central portion thereof with a round opening 5A, and makes it possible to prevent a blood leak under conditions where the catheter 4 is inserted into the path of the main body 2. The second valve body 6 is provided at the central portion there of with a slit 6A, and makes it possible to prevent a blood leak when the catheter 4 is not inserted through the path of the main body 2.

However, a valve body assembly comprising the first valve body 5 and the second valve body 6, an outer diameter of the catheter 4 which is applicable is primarily fixed as commensurate to the round opening 5A formed on the first valve body. In consequence, when only the guide wire is inserted and held in the first valve body 5 and the second valve body 6, a blood leak cannot be prevented, and it becomes difficult to apply to a forward end flexing type catheter requiring a combination of the catheter introducer 1 with the guide wire. Furthermore, in removing the catheter 4 inserted in the main body 2, if the catheter 4 is abruptly withdrawn, then there is a possibility that the slit 6A does not immediately form a suitable closed state and a blood flow-out occurs. Furthermore, this valve body assembly, consisting of the two valve bodies including the first valve body 5 and the second valve body 6, becomes complicated in construction.

In another catheter introducer for medical treatment of the prior art, which has been proposed in Japanese patent application No. 178915/81 (Patent Kokai (Laid-Open) No. 110262/82), such a valve body assembly is used which includes a disc-shaped first valve body having an expandable opening, by which no materials are removed, and a tubular second valve body provided with a forward end portion having sealing lips which are pressed against each other. However, the valve body assembly, being small in scope of expansion or contraction of the opening provided in the first valve body, cannot have tubular members of widely varied outer diameters inserted therethrough and held therein. Furthermore, the valve body assembly, consisting of the two valve bodies including the first valve body and the second valve body, becomes complicated in construction.

In view of the problems accompanied with the prior art, the present inventors have proposed a valve body having a first slit openable in one of the end faces and a second slit openable in the other of the end faces, the first slit and the second slit crossing each other in the valve body (UK patent application No. 2135889A). Since this valve body is dispensed with a first valve 5 having ring-shaped disk as shown in FIG. 1, a catheter of various outer diameters can be applicable thereto without causing leakage of blood. However this valve body has a drawback in that it will take a relatively long time to restore its original closed status after the withdrawal of a catheter, so that a small amount of blood may leak out of the valve body. This tendency is more apparent when a catheter is left in the valve for a long period of time.

SUMMARY OF THE INVENTION

It is an object of the present invention to provide a medical instrument with a valve which at least holds a bar-like member (e.g., hollow cylinders or columnar members having various diameters which are to be inserted or indwelled in a body such as a catheter) while allowing its insertion therethrough such that no liquid leakage occurs, and even after the bar-like member has been left inserted in the valve for a long period of time, a tight seal can be provided when the bar-like member is removed, thus preventing the leakage of blood therefrom.

According to the present invention, there is provided a medical instrument comprising a main body in which a path for receiving a bar-like member is formed, and a valve mounted on the main body and closing the path, the valve has two end faces in the path direction, and having a slit for receiving the bar-like member and, maintaining at least a liquid-tight seal with said bar-like member being passed therethrough, and for closing said path at least in a liquid-tight state when said bar-like member is absent from said path, said valve being made of a flexible and elastic material, wherein the valve comprises a first valve, having a first slit open only to one end face of the valve and a second slit open only to the other end face thereof, the first and second slits extending only partly through said first valve and crossing each other inside the valve so as to connect with each other at their intersection, and a second valve, in parallel and contacting to the first valve and having a slit extending through and open to the two end faces of the second valve.

Furthermore, according to the present invention, there is provided a medical instrument wherein the first and second valves comprise a soft elastic material (e.g., silicone rubber, natural rubber, or sponge).

In the present invention, the bar-like member capable of insertion includes a cathether, a guide wire, the distal end tip portion of a syringe, and a needle.

In this specification, the term "parallel" means that valves are aligned to each other. The two valves can be placed closely together or separated. The term "cross" means that two slits are combined to form an appropriate angle inside the valve, and they connect with each other at the combined portion.

BRIEF DESCRIPTION OF THE DRAWINGS

FIG. 1 is a sectional view showing a conventional medical bar-like member introducer having a valve mechanism;

FIG. 2 is an exploded perspective view of FIG. 1;

FIG. 5(A) is a perspective view showing a first valve in FIG. 3;

FIG. 5(B) is a plan view of the valve in FIG. 5(A);

FIG. 5(C) is a side view of the valve in FIG. 5(A);

FIG. 6 is a diagram for explaining modifications in the direction of slits formed in the valve in FIG. 5(A);

FIG. 9 is a view for explaining an insertion state of the introducer in FIG. 3 showing the introducer, a guide wire, and an extension tube;

FIG. 10 is a view for explaining the introducer shown in FIG. 3 in use;

FIG. 11 is a sectional view of a catheter having the same valve mechanism as in FIG. 4;

FIG. 12 is a sectional view of the main part of FIG. 11;

FIG. 13 is a sectional view of a catheter with a balloon having the same valve mechanism as the introducer in FIG. 4;

FIG. 14 is a sectional view showing the main part of FIG. 13;

FIG. 15 is a sectional view showing an extracorporeal circulator using another combination of the first and second valves shown in FIG. 4;

FIG. 16 is a sectional view showing the main part of FIG. 16;

DETAILED DESCRIPTION OF THE PREFERRED EMBODIMENTS

Figure 3:
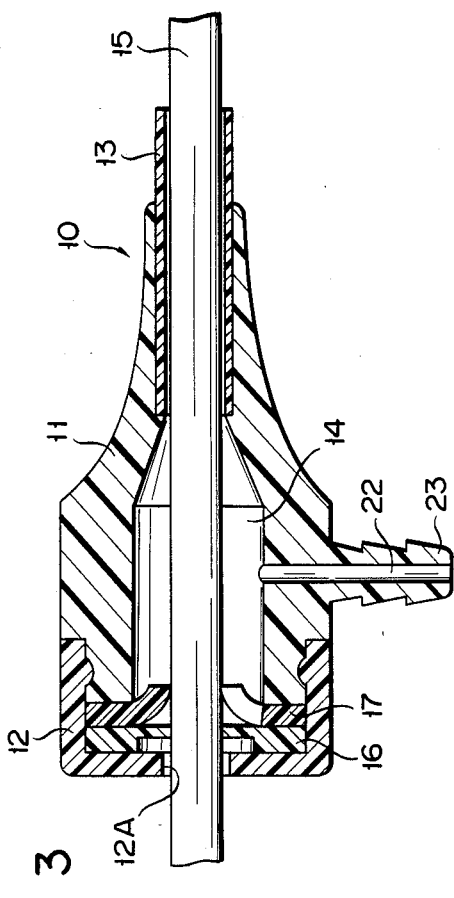
FIG. 3 is a sectional view showing a medical bar-like member introducer having a valve mechanism according to the present invention.
Figure 4:
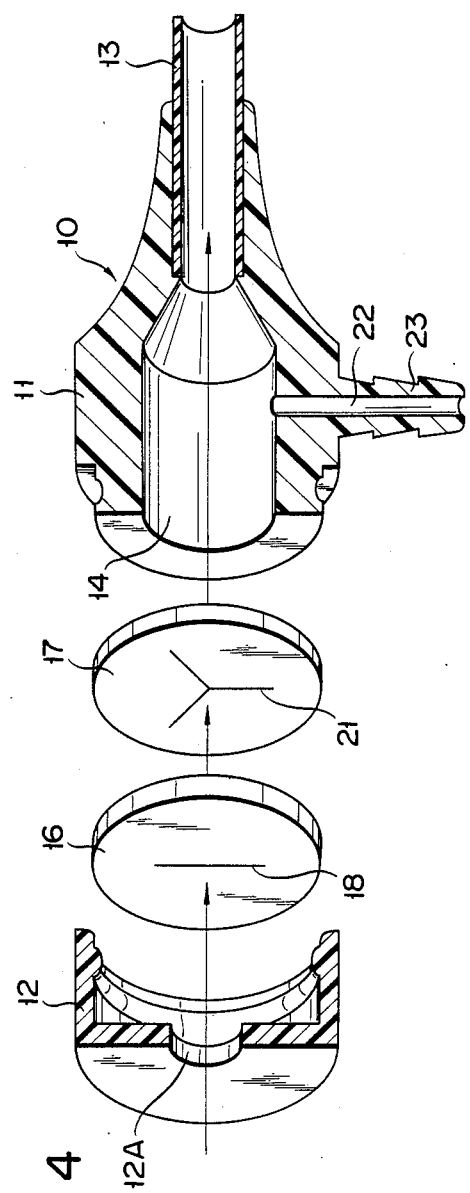
FIG. 4 is an exploded perspective view of FIG. 3.

FIG. 3 is the sectional view showing the catheter intruducer for a medical instrument, to which the first embodiment of the valve body according to the present invention is applied, and FIG. 4 is the disassembled perspective view of FIG. 3. The catheter introducer for the medical instrument 10 comprises a substantially cylindrical main body 11 and a cap 12 coupled to one end of the main body 11 and having an opening 12A. A flexible tube 13 is integrally connected to the tapered end of the main body 11. An axial path or passage 14 is formed in the main body 11 and the flexible tube 13. A catheter 15 can be inserted through the path or passage 14. Provided at one end portion of the main body 11 in a state of being clamped between the main body 11 and the cap 12 are first valve 16 and second valve 17 arranged in a row in an embodiment of the present invention, which form a liquid-tight state in cooperation with the catheter 15 inserted through the path 14 and closes the path 14 when the catheter 15 is not inserted.

The first valve 16 and second valve 17 are respectively made of a flexible and elastomeric material including a synthetic rubber such as a silicone rubber, urethane rubber or a fluororubber, and a natural rubber, etc.

Figure 7:
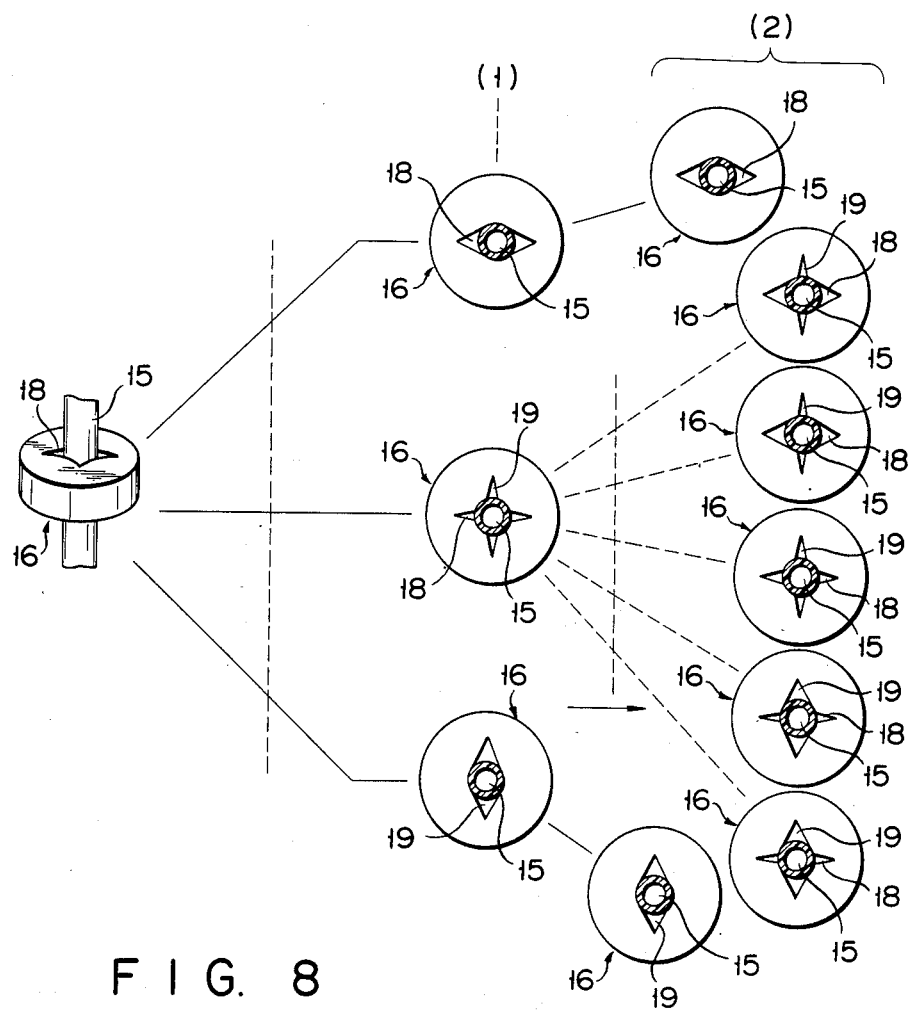
FIG. 7 is a view for explaining opening shapes of the slits formed in the valve in FIG. 5(A)

As shown in FIGS. 5(A) through 5(C), the valve body 16 is formed therein in a suitable method with a first slit 18 openable to one of the end faces thereof and a second slit 19 openable to the other of the end faces thereof. The first slit 18 and the second slit 19 cross each other at the inside of the valve body 16. The term "cross" means that the slits are combined together alternately, whereby the slits formed from opposite end faces partially coincide with each other at the crossing portion, so that the rod-like members are insertable. In addition, the angle of crossing need not necessarily be a right angle. More specifically, the first slit 18 and the second slit 19 form a crossing portion 20 having a distance L. In consequence, the catheter 15 is made passable through the first slit 18, the second slit 19 and the crossing portion 20 formed therebetween under an elastic deformation of the valve body 16. FIG. 6 is the explanatory view showing the direction (the direction of arrow) of deformation of the first slit 18 and the second slit 19 when the catheter 15 is inserted through the valve body 16. FIG. 7 is the explanatory view showing the shapes of openings in the first slit 18 and the second slit 19 when the catheter 15 is inserted through the valve body 16. If the valve body 16 is sliced into three characteristic portions in the axial direction thereof, including a portion having therein only the first slit 18, a portion having therein a crossing portion 20 and a portion having therein only the second slit 19, then there exist three portions 16A through 16C as shown in (1) of FIG. 6. If, in the valve body 16, three separate portions as shown at the 16A through 16C are merely superimposed on one another, then the directions of deformation of the slits 18 and 19 when the insertion is about to be made become ones as indicated by arrow marks in (2) of FIG. 6, and shapes of openings of the slits 18 and 19 after the insertion become ones shown in (1) of FIG. 7. However, since the valve body 16 is originally an integral body by itself, each of the sliced portions is subject to the influences from the other portions adjacent thereto, the directions of deformation of the slits 18 and 19, when the catheter 15 is about to be inserted, are continuously varied inside the valve body 16 along the axial direction thereof as indicated by arrow marks in (3) of FIG. 6, and the shapes of openings of the slits 18 and 19 after the insertion become ones shown in (2) of FIG. 7. More specifically, the surroundings of the catheter 15 inserted through the valve body 16 are continuously pressed by the slits 18 and 19 along the axial direction of the valve body 16 with no gaps being formed even when the outer diameter of the catheter 15 is comparatively small or comparatively large. Since the valve body 16 is made of the flexible and elastomeric material as aforesaid, the slits 18 and 19 come into close surface-to-surface contact with the outer peripheral portion of the catheter 15, to thereby form a reliable liquid-tight or air-tight state between the catheter 15 and the valve body 16. In addition, a distance L formed by the crossing portion 20 between the first slit 18 and the second slit 19 is determined in accordance with the maximal outer diameter of the catheter 15 to be inserted into the valve body 16. Preferably, the length of L should be 0.4 mm or more.

Figure 8:
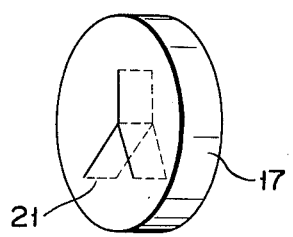
FIG. 8 is a perspective view of a second valve shown in FIG. 3.

Radial slit 21 (e.g., a Y-shaped slit) is formed in second valve 17, as shown in FIG. 8. Since second valve 17 is separated from first valve 16, when a bar-like member (e.g., a catheter) is inserted into slit 21, slit 21 is opened and turned over in the insertion direction of the member.

Connecting portion 23 forming path 22 communicating with path 14 is molded integrally with medical instrument 10. If a heparin-containing normal saline solution is introduced into appliance 10, thrombus in path 14 or at the boundary between path 14 and catheter 15 can be prevented.

DETAILED OPERATION OF THE INVENTION

A method of using medical instrument 10, which comprises a combination of first and second valves 16 and 17, will be described hereafter with reference to FIGS. 9 and 10. Prior to use of instrument 10, a hollow needle in which an inner needle is inserted penetrates the skin and is introduced into a blood vessel. After removing the inner needle from the hollow needle, guide wire 31 is inserted into the hollow needle. When the hollow needle is removed, one end of guide wire 31 remains indwelled in the blood vessel. As shown in FIG. 9, extension device 32, which is inserted in path 14, is fitted to cover guide wire 31. The distal end portion of device 32 is guided along guide wire 31 and inserted into the blood vessel wall, thereby extending the hole in the blood vessel wall. Then, flexible tube 13 of instrument 10 is introduced into blood vessel 33. Device 32 and guide wire 31 are removed while a heparin-containing normal saline solution is supplied in path 14 through supply tube 34 connected to connecting portion 23. When guide wire 31 and device 32 are inserted in path 14 of instrument 10, first valve 16 is brought into surface contact with device 32 and forms a tight seal, thus preventing blood leakage. When wire 31 and device 32 are removed from path 14 of instrument 10, second valve 17 is returned from the turned over state to its original closed state. Furthermore, first and second slits 18 and 19 of first valve 16 are also closed, thus preventing blood leakage. After wire 31 and device 32 are removed and only flexible tube 13 of instrument 10 remains indwelled in vessel 33, first and second slits 18 and 19 of valve 16 and slit 21 of valve 17 are completely closed, thereby preventing blood leakage.

Since slits 18 and 19 of first valve 16 do not reach the corresponding opposite end faces, they can provide high pressure resistance against blood pressure applied to an end face of valve 16 and maintain a tight seal without being deformed by the blood pressure.

Catheter 15 is then introduced via opening 12A of cap 12, and penetrates through slits 18 and 19 of valve 16 and slit 21 of valve 17. Catheter 15 passes through main body 11, is guided to flexible tube 13, and then reaches vessel 33. When catheter 15 is inserted into path 14 of instrument 10, valve 16 is brought into surface contact with catheter 15 and forms a tight seal, thus preventing blood leakage. When catheter 15 has reached a predetermined position, a given medical operation (e.g., angiographic X-ray imaging) can be conducted.

When catheter 15 is removed from instrument 10, catheter 15 is pulled out from slit 21 of valve 17, and at the same time a completely tight seal is immediately formed due to the strong recovery force of valve 17. Catheter 15 is then pulled out from slits 18 and 19 of valve 16, and these slits also form a completely tight seal, thus preventing blood leakage.

Since slits 18 and 19 of valve 16 are open to the corresponding opposite end faces of valve 16, they will not open the opposite slits when catheter 15 is removed.

According to the above embodiment, slits 18 and 19 of valve 16 can be brought into tight contact with catheters having various diameters. Therefore, when a catheter has been introduced into a vessel, only a guide wire can be inserted and held in instrument 10. In addition, a catheter with a bent distal end can be introduced into a blood vessel in a liquid tight state even when instrument 10 and a guide wire are used together with the catheter.

FIG. 11 is a sectional view showing a catheter comprising first and second valves 16 and 17 at its base end opening as another application of a combination of valves 16 and 17, and FIG. 12 is a sectional view showing the main part thereof.

In this application, first and second valves 16 and 17 are clamped between plug 41 and cap 42, which is fitted in one end portion of plug 41. Plug 41 comprises tapered outer surface 46 detachable from tapered opening inner surface 45 of hub 44, which constitutes the base end portion of indwellable blood vessel catheter 43. In addition, plug 41 comprises path 48 communicating with path 47 of catheter 43. Cap 42 has path 42A. Note that reference numeral 49 denotes a guide wire.

A method of using catheter 43 comprising first and second valves 16 and 17 will be described hereinafter. Prior to the use of catheter 43, a hollow needle in which an inner needle is inserted penetrates the skin and is introduced into a blood vessel. After the inner needle is removed from the hollow needle, guide wire 49 is inserted through the hollow needle. The hollow needle is then removed, leaving one end of guide wire 49 in the blood vessel. When plug 41 with valves 16 and 17 is fitted in hub 44 of catheter 43, wire 49 is fitted in path 47 of catheter 43. Catheter 43 is guided along wire 49 and introduced into the blood vessel. Thus, when catheter 43 is introduced into the blood vessel, blood flowing through the vessel flows into path 47 of catheter 43. However, plug 41, having valves 16 and 17, is fitted in hub 44 provided at the base end portion of catheter 43, and first and second slits 18 and 19 of valve 16 and slit 21 of second valve 17 are sealed. Therefore, blood cannot escape from the base end opening of catheter 43. Since second valve 17 is provided in addition to first valve 16 having high pressure resistance as described above, they can maintain a tight seal without being deformed by blood pressure.

During the introduction of cathether 43 into the blood vessel, slits 18 and 19 of valve 16 mounted on the base end opening of catheter 43 are brought into surface contact with the periphery of wire 49 and form a tight seal, thus preventing blood leakage.

When the distal end portion of catheter 43 has reached a predetermined position in the blood vessel, wire 49 is removed from path 47 of catheter 43. Wire 49 is pulled out from slit 21 of valve 17, and at the same time, a perfectly tight seal is formed by slit 21, thereby preventing blood leakage. When wire 49 is then pulled out from slits 18 and 19 of valve 16, they also form a tight seal. Therefore, when wire 49 is removed from path 47 of catheter 43 and only catheter 43 remains indwelled in the blood vessel, blood leakage can be completely prevented by first and second valves 16 and 17.

In order to inject a blood vessel contrast medium into the blood vessel through path 47 of catheter 43, an injection tip is inserted into path 47 of catheter 43 through valve 16, and the contrast medium is injected into path 47 of catheter 43. In this manner, when the injection tip of an injector passes through valve 16, slits 18 and 19 of valve 16 are brought into surface contact with the periphery of the injection tip and form a tight seal, thus preventing blood leakage. When the injection tip of the injector is removed from valves 16 and 17, slit 21 of valve 17 immediately forms a tight seal to prevent blood leakage. Since slits 18 and 19 can form a tight seal with the periphery of a bar-like member irrespective of the diameter of the bar-like member inserted, leakage is prevented even though wire 49 and the injection tip of the injector have different diameters.

After completion of contrast medium injection, the injection tip of the injector is removed from valves 16 and 17, and wire 49 is re-inserted into valve 16 and catheter 43. Wire 49 acts as a guide for catheter 43 and both are removed from the blood vessel, thus completing the angiographic operation.

FIG. 13 is a sectional view showing another application of a combination of first and second valves 16 and 17, wherein a catheter with a balloon comprises first valves 16X and 16Y having the same arrangement as valve 16, and second valves 17X and 17Y having the same arrangement as valve 17; and FIG. 14 is an enlarged sectional view of the main part thereof. Main body 51 of catheter 50 with a balloon comprises flexible straight portion 51A and branch portion 51B, formed at the base end side of portion 51A. Portion 51A has main path 52 passing therethrough from the base end side to the distal end side. A guide wire can be inserted in path 52 to introduce catheter 50 into a blood vessel. In addition, path 52 allows drugs to pass therethrough. It should be noted that main hub 53 is mounted at the base end of portion 51A.

Balloon 54, of an elastic material which can be expanded from a contracted state, is provided on the outer periphery of portion 51A of body 51. Subpath 55, communicating with the inside of balloon 54 from the base end side of portion 51B, is formed in portions 51A and 51B. Y-shaped subhub 56 is connected to portion 51B of body 51, and first and second subpaths 56A and 56B communcating with subpath 55 are formed in subhub 56. A pair of valves 16X and 17X, into which a fine outlet tube can be inserted, are mounted on the base end opening of subpath 56A. A pair of valves 16Y and 17Y, into which an injector for injecting a balloon expansion liquid can be inserted, are mounted on the base end opening of subpath 56B. Valves 16X, 17X, 16Y, and 17Y are held by caps 57 and 58 fitted in subhub 56. Paths 57A and 57B are formed in caps 57 and 58.

A method of using catheter 50 comprising first and second valves 16X, 16Y, 17X, and 17Y will be described hereinafter. Prior to the use of catheter 50, a hollow needle in which an inner needle is inserted penetrates the skin and is introduced into a blood vessel. After the inner needle is removed from the hollow needle, a guide wire is inserted through the hollow needle. The hollow needle is then removed, leaving one end of the guide wire in the blood vessel. The guide wire is inserted into path 52 of catheter 50 to guide catheter 50 into the blood vessel, thereby guiding contracted balloon 54 to a predetermined position in the blood vessel at which it is to be expanded.

The fine outlet tube is then inserted into path 57A of cap 57, slits 18 and 19 of valve 16X, slit 21 of valve 17X, and subpath 56A until its distal end reaches the part of subpath 55 at which balloon 54 is to be disposed. The injector for injecting a balloon expansion liquid (e.g., normal saline solution) is inserted into path 58A of cap 58, slits 18 and 19 of valve 16Y, and slit 21 of valve 17Y, thereby injecting the liquid into subpaths 55, 56A, and 56B, and removing any air therein through the outlet tube. In this case, slits 18 and 19 of valves 16X and 16Y are brought into surface contact with the periphery of the outlet tube or injector and form a tight seal, thus preventing blood leakage.

After the air in subpaths 55, 56A, and 56B is removed, the outlet tube is removed from subpaths 55 and 56A. The expansion liquid is then continuously injected into subpaths 55, 56A, and 56B to expand balloon 54 to a predetermined state. Thereafter, the injector is also removed, and a given medical operation is conducted by expanded balloon 54. When the outlet tube and the injector are removed from slits 21 of valves 17X and 17Y, slits 21 simultaneously form a perfectly tight seal, thus preventing liquid leakage. When the outlet tube and the injector are removed from valves 16X and 16Y, slits 18 and 19 are also sealed tightly. During this operation, therefore, liquid leakage can be almost completely prevented.

FIG. 15 is a sectional view showing a circulation pipe portion of an extracorporeal circulator, which comprises a structure capable of mounting a sensor (e.g., a temperature sensor) as another application of a combination of first and second valves 16 and 17; and FIG. 16 is a sectional view showing a sensor mounting structure thereof. In extracorporeal circulator 60, connecting pipe 63 is fitted in the central portion between first pipe 61, connected to a blood vein in a human body, and second pipe 62, connected to an artery. Pipes 61, 62, and 63 respectively comprise paths 61A, 62A, and 63A communicating with each other and constituting a circulation pipe. An artificial lung or a blood pump is fitted around an intermediate portion (not shown) of pipe 61 or 62. Pipe 63 comprises insertion path 63B, perpendicular to path 63A, for inserting sensor 64 into path 63A. First and second valves 16 and 17 are disposed on an opening of path 63B so that valve 16 is provided inside of valve 17, in contrast to the above embodiment. Valves 16 and 17, through which sensor 64 can be inserted into paths 63A and 63B, define the interior of the circulation pipe and are closed when sensor 64 is not inserted therein. Valves 16 and 17 are provided on the opening of path 63B so that they are in tight contact with each other, and are clamped between pipe 63 and cap 65 fitted therein. Path 65A, in which sensor 64 can be inserted, is formed in cap 65.

A method of using circulator 60 comprising valves 16 and 17 will now be described.

When circulator 60 having an artificial lung or a blood pump is connected to a human body, blood circulates through paths 61A, 62A, and 63A of pipes 61, 62, and 63. Since valves 16 and 17 are disposed on path 63B of pipe 63 and first and second slits of valve 16 and slit 21 of valve 17 are closed, blood cannot escape from path 63B of path 63.

When the blood circulating through circulator 60 is tested to determine if appropriate gas exchange is being performed, sensor 64 corresponding to a test item is inserted into paths 63B and 63A of pipe 63 through path 65A of cap 65, slit 21 of valve 17, and slits 18 and 19 of valve 16. Thus, oxygen partial pressure, carbon dioxide partial pressure, pH, etc. in the blood can be continuously detected. Slits 18 and 19 of valve 16 are brought into surface contact with the periphery of sensor 64 and form a tight seal, thus preventing blood leakage.

When sensor 64 completes a desired detecting operation, or when thrombus becomes attached to sensor 64 positioned inside of pipe 63 and sensor 64 must be exchanged, sensor 64 is pulled out from slits 18 and 19 of valve 16 and slit 21 of valve 17. Slits 18 and 19 are tightly sealed when sensor 64 is removed therefrom, thus preventing blood leakage. In addition, slit 21 of valve 17 also forms a tight seal immediately because of its strong recovery force. Therefore, blood leakage can be almost completely prevented.

With circulator 60 of this embodiment, sensor 64 can be indwelled in pipe 63, and oxygen partial pressure, carbon dioxide partial pressure, pH, etc. in the blood can be continuously detected, thus guaranteeing the safety of a patient. Since sensor 64 can be mounted in pipe 63 after circulator 60 is connected to a patient, the pipe system can be easily dealt with. Sensor 64 can easily be removed from pipe 63 during extracorporeal circulation. For example, if thrombus becomes attached to sensor 64, the sensor can quickly be replaced with a new one. Slits 18 and 19 can be brought into surface contact with the periphery of sensor 64 and form a tight seal irrespective of the diameter of sensor 64.

In the above embodiment, an internal cross slit type first valve having two linear slits formed in two end faces of the valve to cross each other, and a second valve having a Y-shaped slit which passes through the valve from one end face to the other end face have been described. As for the first valve, each slit must be formed from the two end faces so as not to penetrate the soft elastic member so that they cross each other at an appropriate length. There are no other limitations. As for the second valve, the slit need only be formed from one end face of the soft elastic member to reach the other end face. When a bar-like member (e.g., a catheter) is inserted in the first valve, the portion near the inserted member extends in the circumferential direction, and the valve applies its recovery force to the bar-like member in the axial direction. Therefore, the valve can achieve a perfectly tight seal with the periphery of the bar-like member, thus preventing liquid leakage. When the bar-like member is inserted in the second valve, since the portion near the inserted member is turned over in the insertion direction, the valve can be recovered immediately. Therefore, when the bar-like member is removed, liquid leakage can be effectively prevented. Since valves having two different types of slits are combined, a tight seal and the prevention of liquid leakage can both be accomplished while compensating for individual defects.

Modifications of the first and second valves of the present invention will be described with reference to the drawings.

Figure 17A:
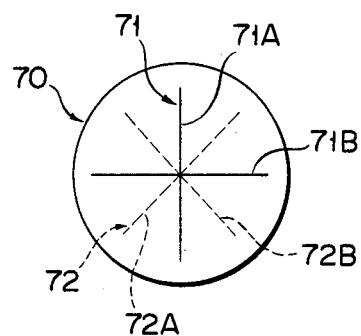
FIG. 17(A) is a plan view showing a first modification of the first valve of the present invention.
Figure 17B:
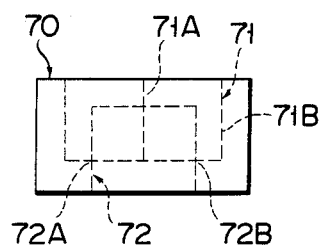
FIG. 17(B) is a side view of FIG. 17(A)

In first valve 70 shown in FIGS. 17(A) and 17(B), first slit 71 is constituted by slits 71A and 71B crossing each other, and second slit 72 is constituted by slits 72A and 72B crossing each other. First and second slits 71 and 72 cross so that respective crossing portions overlap each other inside valve 70. With valve 70 of this modification, even when the lengths of slits 71 and 72 are small, the deformation properties of slits 71 and 72 can be enhanced. Therefore, a bar-like member having a relatively large diameter can be inserted in valve 70 despite its relatively small dimensions.

Figure 18A:
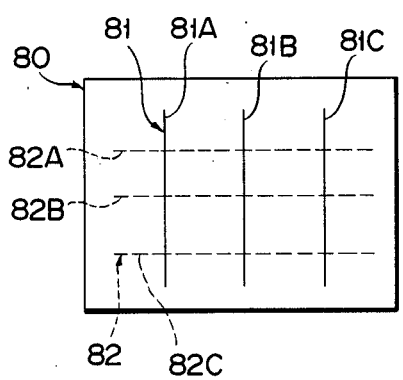
FIG. 18(A) is a plan view showing a second modification of the first valve of the present invention.
Figure 18B:
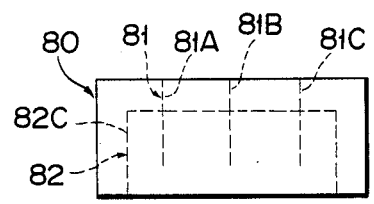
FIG. 18(B) is a side view of FIG. 18(A)

In first valve 80 shown in FIGS. 18(A) and 18(B), first slit 81 comprises slits 81A, 81B, and 81C which do not cross each other, and second slit 82 comprises slits 82A, 82B, and 82C which do not cross each other. First and second slits 81 and 82 cross at nine positions inside valve 80. With valve 80 of this modification, a maximum of nine bar-like members can be simultaneously inserted and held.

Figure 19A:
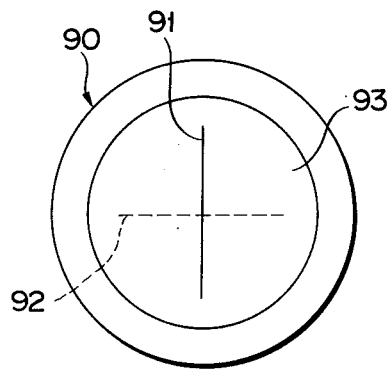
FIG. 19(A) is a plan view showing a third modification of the first valve of the present invention.
Figure 19B:
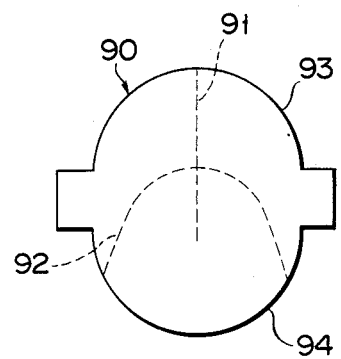
FIG. 19(B) is a side view of FIG. 19(A)

First valve 90 shown in FIGS. 19(A) and 19(B) has first and second slits 91 and 92, and end faces 93 and 94 project outward. Therefore, blood pressure applied to the end face is concentrated on the central portion of valve 90, and a tight seal with respect to a bar-like member can be reliably formed.

Figure 20:
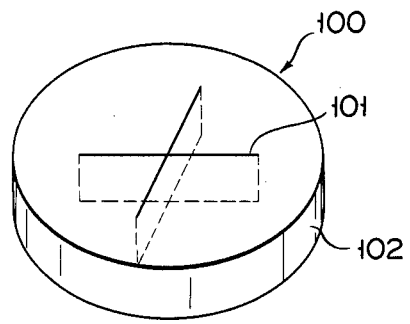
FIG. 20 is a perspective view showing a modification of the second valve of the present invention.

Second valve 100 shown in FIG. 20 has cross-shaped slit 101 which passes through two end faces of disk-like soft elastic member 102, thus allowing insertion of a bar-like member having a larger diameter than that of FIG. 8.

The first and second valves can be combined so that a slit crossing portion of the first valve overlaps a substantially central portion (in a lengthwise direction) of a slit of the second valve. Therefore, the slits of the first and second valves can overlap linearly.

(EXAMPLE)

Figure 21:
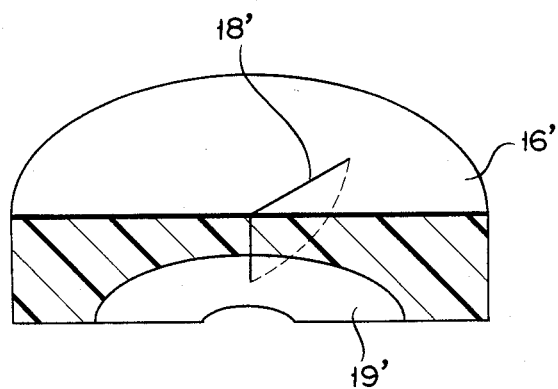
FIG. 21 is a partially cutaway perspective view showing another modification of the second valve of the present invention.

As shown in FIG. 21, internal cross slit type disk 16' comprises a disk-shaped elastic member having a diameter of 8 mm and a height of 1.5 mm, wherein first and second arc-shaped slits 18' and 19' (length, 5.0 mm; a depth at a central point, 1.0 mm; and crossing length, 0.5 mm) are formed from two end faces of disk 16' to cross each other. Disk 16' was used as a first valve. A disk-shaped elastic member (height, 0.9 mm; diameter, 8 mm) having a Y-shaped slit whose branch slits extend linearly from the center of the member for a distance of 2.5 mm in three different directions, as shown in FIG. 8, was used as a second valve. These valves were mounted in a medical instrument as shown in FIG. 3 (to be referred to as sample A hereinafter). Note that the first and second valves were made of silicone rubber (available from Dow-Corning Corp., trade name Q7-4735).

Furthermore, only disk 16' (first valve) was mounted in a medical bar-like member introducer as a comparative sample (to be referred to as sample B hereinafter).

A large number of such samples A and B were prepared. A pneumatic pressure of 0.3 to 0.4 $kg/cm^2$ was applied to the interior of path 14 while sealing the distal end of flexible pipe 13, and catheters having outer diameters of 3 Fr to 8 Fr were inserted 10 cm below the water surface, thus checking the presence/absence of air leakage in each sample.

No air leakage was found in any sample A when catheters were inserted or removed, irrespective of catheter diameters. However, slight air leakage was found in samples B when catheters with outer diameters of 3 Fr to 5 Fr were inserted.

Furthermore, a pressure corresponding to a 2-m water column was applied to the interior of path 14, and water leakage was checked when catheters were removed. In samples A, no leakage occured. However, in samples B, water leakage was found at a ratio of 1 : 10.

The medical instrument with valves according to the present invention comprises a combination of a first valve, in which a first slit open to one end face of the valve and a second slit open to the other end face thereof are formed, such that the first and second slits cross each other inside the valve, and a second valve, having a slit open to two end faces thereof. Therefore, the valves can receive and hold bar-like members having various diameters in a liquid tight state, and can be immediately recovered to an appropriate closed state when the bar-like member is removed.

In the present invention, three or more valves including a first valve can be combined.

What is claimed is:

1. A medical instrument comprising a main body, in which a path for receiving a bar-like member is formed and a valve mounted on said main body and closing said path, the valve has two end faces in the path direction and having a slit for receiving said bar-like member and, maintaining at least a liquid-tight seal with said bar-like member being passed therethrough, and for closing said path at least in a liquid-tight state when said bar-like member is absent from said path, said valve being made of a flexible and elastic material, wherein said valve comprises a first valve, having a first slit open only to one end face of said valve and a second slit open only to the other end face thereof, said first and second slits extending only partly through said first valve and crossing each other inside said first valve to connect with each other at their intersection, and a second valve, in parallel and contacting to said first valve and having a slit extending through and open to two end faces of said second valve.

2. A medical instrument according to claim 1, wherein said soft elastic material comprises a material selected from the group consisting of silicone rubber, natural rubber, and sponge.

3. A medical instrument according to claim 1, wherein said first valve has a disk shape with a height of not less than 1 mm, and said first and second slits cross at a length of not less than 0.4 mm.

4. A medical instrument according to claim 1, wherein said slit of said second valve is a radial slit, and a center thereof overlaps the intersection of the slits of said first valve.

5. A medical instrument according to claim 1, wherein a branch port communicating with a bar-like member insertion path is connected to said main body.

6. A medical instrument according to claim 1, wherein said first and second valves are provided close together and parallel to each other.

7. A medical instrument according to claim 1, wherein said first and second slits of said first valve are arcuated slits.

8. A medical instrument according to claim 1, wherein said first slit of said first valve comprises a plurality of slits crossing each other, said second slit thereof comprises a plurality of slits crossing each other, and said first and second slits cross inside said first valve so that individual intersections overlap each other.

9. A medical instrument according to claim 1, wherein said first slit of said first valve comprises a plurality of slits which do not cross each other, said second slit thereof comprises a plurality of slits which do not cross each other, and said first and second slits cross at a plurality of positions inside said first valve.

10. A medical instrument according to claim 1, wherein at least one end face of said first or second valve has a projecting surface.

* * * * *